(12) United States Patent
Sick et al.

(10) Patent No.: US 11,399,771 B2
(45) Date of Patent: Aug. 2, 2022

(54) IMPLANTABLE MONITOR INTRODUCER

(71) Applicant: Cardiac Pacemakers, Inc., St. Paul, MN (US)

(72) Inventors: Kathryn Sick, Shoreview, MN (US); Keith R. Maile, New Brighton, MN (US); Britta C. Veldman, White Bear Township, MN (US); Arthur J. Foster, Blaine, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 1043 days.

(21) Appl. No.: 15/728,891

(22) Filed: Oct. 10, 2017

(65) Prior Publication Data

US 2018/0125424 A1   May 10, 2018

Related U.S. Application Data

(60) Provisional application No. 62/420,419, filed on Nov. 10, 2016.

(51) Int. Cl.
| | | |
|---|---|---|
| *A61B 5/00* | (2006.01) | |
| *A61B 17/3209* | (2006.01) | |
| *A61B 5/0538* | (2021.01) | |
| *A61B 90/00* | (2016.01) | |
| *A61B 17/3211* | (2006.01) | |

(Continued)

(52) U.S. Cl.
CPC ............ *A61B 5/686* (2013.01); *A61B 5/0538* (2013.01); *A61B 5/068* (2013.01); *A61B 5/283* (2021.01); *A61B 17/3209* (2013.01); *A61B 17/3211* (2013.01); *A61B 17/32093* (2013.01); *A61B 90/03* (2016.02); *A61B 90/06* (2016.02); *A61B 17/3494* (2013.01); *A61B 2017/320052* (2013.01); *A61B 2090/061* (2016.02); *A61B 2090/062* (2016.02); *A61B 2560/063* (2013.01)

(58) Field of Classification Search
CPC ....... A61B 5/0531; A61B 5/068; A61B 5/042; A61B 2090/061; A61B 2090/06; A61B 2017/00455
See application file for complete search history.

(56) References Cited

U.S. PATENT DOCUMENTS

| 2,932,296 A | 4/1960 | Sanders |
|---|---|---|
| 3,945,117 A | 3/1976 | Beaver |

(Continued)

FOREIGN PATENT DOCUMENTS

| CN | 102215904 A | 10/2011 |
|---|---|---|
| CN | 104837419 A | 8/2015 |

(Continued)

OTHER PUBLICATIONS

International Search Report and Written Opinion issued in PCT/US2017/055884, dated Jan. 16, 2018, 14 pages.

*Primary Examiner* — Linda C Dvorak
*Assistant Examiner* — Christine A Dedoulis
(74) *Attorney, Agent, or Firm* — Faegre Drinker Biddle & Reath LLP

(57) ABSTRACT

Various aspect of the present disclosure are directed toward apparatuses, systems, and methods that may include an introducer for facilitating placement of an implantable monitor. The introducer may include an indicator configured to indicate at least one of width, depth, and position for an arrangement of the implantable monitor relative to a patient.

13 Claims, 5 Drawing Sheets

(51) Int. Cl.
*A61B 5/283* (2021.01)
*A61B 5/06* (2006.01)
A61B 17/32 (2006.01)
A61B 17/34 (2006.01)

(56) References Cited

U.S. PATENT DOCUMENTS

| | | | | |
|---|---|---|---|---|
| 6,972,022 | B1* | 12/2005 | Griffin | A61B 90/39 604/112 |
| 8,219,200 | B2 | 7/2012 | Wenger et al. | |
| 8,224,447 | B2 | 7/2012 | Wenger et al. | |
| 9,084,872 | B2 | 7/2015 | Rooney et al. | |
| 9,242,108 | B2 | 1/2016 | Wengreen et al. | |
| 9,402,607 | B2* | 8/2016 | Smits | A61N 1/05 |
| 10,383,609 | B2* | 8/2019 | Nakanishi | A61B 17/32 |
| 2004/0236315 | A1* | 11/2004 | Hered | A61B 90/39 606/1 |
| 2005/0131391 | A1* | 6/2005 | Chu | A61B 17/00234 606/1 |
| 2009/0036917 | A1 | 2/2009 | Anderson | |
| 2010/0094252 | A1 | 4/2010 | Wengreen et al. | |
| 2010/0331874 | A1 | 12/2010 | Bardy | |
| 2013/0079608 | A1 | 3/2013 | Miller et al. | |
| 2013/0324977 | A1 | 12/2013 | Vanderpool | |
| 2013/0324980 | A1 | 12/2013 | Martin | |
| 2014/0276928 | A1 | 9/2014 | Vanderpool et al. | |
| 2015/0209588 | A1 | 7/2015 | Christensen | |
| 2017/0049352 | A1* | 2/2017 | Mirov | A61B 5/0533 |
| 2017/0086803 | A1 | 3/2017 | Nakanishi et al. | |

FOREIGN PATENT DOCUMENTS

| | | |
|---|---|---|
| GB | 2113550 A | 8/1983 |
| WO | 2011044386 A1 | 4/2011 |
| WO | 2016103366 A1 | 6/2016 |

* cited by examiner

IMPLANTABLE MONITOR INTRODUCER

CROSS-REFERENCE TO RELATED APPLICATION

This application claims priority to Provisional Application No. 62/420,419, filed Nov. 10, 2016, which is herein incorporated by reference in its entirety.

TECHNICAL FIELD

The present disclosure relates to medical devices and methods for creating a pocket in a patient for an implantable monitor. According to embodiments, the disclosure relates to devices and methods for facilitating placement of an implantable monitor.

BACKGROUND

Medical devices may be implanted subcutaneously under a patient's skin with minimal intervention and without deeply positioning the device in the patient's body. Improperly positioning functional aspects of the device may result in poor performance. This may include, for example, forming a pocket that is too large for the medical device, forming a pocket having improper dimensions, and/or implanting the medical device at an improper location. Thus, there is a need for an introducer device that facilitates pocket formation and positioning of an implantable monitor relative to the patient.

SUMMARY

In Example 1, an introducer for facilitating placement of an implantable monitor, the introducer including: a body portion; and an indicator cooperating with the body portion and configured to indicate at least one of width, depth, and position for an arrangement of the implantable monitor relative to a patient.

In Example 2, the introducer of Example 1, wherein the indicator includes a measurement scale arranged on an upper surface of the body portion, and the measurement scale indicates the width for the arrangement of the implantable monitor.

In Example 3, the introducer of any of Examples 1 or 2, wherein the width is at least approximately equal to a width of the implantable monitor.

In Example 4, the introducer of any of Examples 1-3, wherein the indicator includes a gap on the body portion arranged between a first side wall and a second side wall, and the gap is configured to limit the width for the arrangement of the implantable monitor.

In Example 5, the introducer of Example 4, wherein the gap includes an upper boundary, and the upper boundary forms a portion of a top surface of the body portion.

In Example 6, the introducer of Example 4, wherein the first side wall and the second side wall are configured to limit the depth for the arrangement of the implantable monitor.

In Example 7, the introducer of any of Examples 1-6, wherein the indicator is a separable indicator configured to interface and cooperate with the body portion.

In Example 8, the introducer of Example 7, wherein the separable indicator is configured to indicate the depth for the arrangement of the implantable monitor In Example 9, the introducer of Example 8, wherein the separable indicator is configured to surround a blade of a scalpel and control a length of the blade that protrudes through the depth limiter.

In Example 10, the introducer of any of Examples 1-9, wherein the indicator is configured to sense an impedance measurement of the patient and indicate the position for the arrangement of the implantable monitor in response thereto.

In Example 11, the introducer of Example 10, further including at least one visual aid arranged on an upper surface of the body portion, and the at least one visual aid is configured to direct a clinician to an operative position in response to the impedance measurement sensed by the indicator.

In Example 12, the introducer of any of Examples 1-9, wherein the indicator includes one or more electrical contacts configured to interface with one or more electrodes of the implantable monitor and determine an operative position for the arrangement of the implantable monitor and indicate the position for the arrangement of the implantable monitor.

In Example 13, the introducer of any of Examples 1-12, wherein the body portion includes a first section and a second section, the first section including at least one gripping portion tapering inwardly toward a center of the body portion.

In Example 14, the introducer of Example 12, wherein the second section is arranged perpendicular to the first section and includes a size and shape equal to a size and shape of the implantable monitor.

In Example 15, the introducer of any of Examples 1-14, wherein a lower surface of the body portion includes a stamp to indicate an operative position for the implantable monitor onto skin of a patient.

In Example 16, an introducer for facilitating placement of an implantable monitor, the introducer including: a body portion; and an indicator cooperating with the body portion and configured to indicate at least one of (1) a width for an incision into the skin of a patient, (2) a depth for the incision within the patient, and (3) a position for the implantable monitor within the patient.

In Example 17, the introducer of Example 16, wherein the indicator includes a measurement scale arranged on an upper surface of the body portion, and the measurement scale indicates the width for the incision for the arrangement of the implantable monitor within the patient.

In Example 18, the introducer of Example 17, wherein the indicator includes a gap on the body portion arranged between a first side wall and a second side wall, and the gap is configured to limit the width for the incision for the arrangement of the implantable monitor within the patient.

In Example 19, the introducer of Example 18, wherein the gap includes an upper boundary, and the upper boundary forms a portion of a top surface of the body portion.

In Example 20, the introducer of Example 19, wherein the gap is configured to limit the depth for the incision and the width for the incision for the arrangement of the implantable monitor within the patient.

In Example 21, the introducer of Example 20, wherein the gap is configured to pass a scalpel therethrough and guide the depth for the incision and the width for the incision.

In Example 22, the introducer of Example 19, further including a cutter configured to form an incision in the patient and interface with the body portion, wherein the gap is configured to limit the depth for the incision.

In Example 23, the introducer of Example 22, wherein the cutter includes one or more electrical contacts configured to interface with one or more electrodes of the implantable monitor and determine an operative position for the arrangement of the implantable monitor and indicate the position for the arrangement of the implantable monitor In Example 24, the introducer of Example 16, wherein the indicator is configured to sense an impedance measurement of the patient and indicate the position for the arrangement of the implantable monitor in response thereto.

In Example 25, the introducer of Example 24, further including at least one visual aid arranged on an upper surface the body portion, and the at least one visual aid is configured to direct a clinician to move the implantable monitor to an operative position in response to the impedance measurement sensed by the indicator.

In Example 26, the introducer of Example 16, wherein the indicator includes one or more electrical contacts configured to interface with one or more electrodes of the implantable monitor and determine an operative position for the arrangement of the implantable monitor and indicate the position for the arrangement of the implantable monitor.

In Example 27, the introducer of Example 16, wherein the body portion includes a first section and a second section, the first section including at least one gripping portion tapering inwardly toward a center of the body portion.

In Example 28, the introducer of Example 27, wherein the second section is arranged perpendicular to the first section and includes a size and shape at least approximately equal to a size and shape of the implantable monitor.

In Example 29, the introducer of Example 16, wherein a lower surface of the body portion includes a stamp to indicate an operative position for the implantable monitor onto skin of a patient.

In Example 30, an introducer system including: an implantable monitor; a body portion having a proximal portion including a proximal opening and distal portion including a distal opening, the proximal portion and the distal portion separating an intermediate portion sized to contain the implantable monitor; an ejection rod configured to pass through the proximal opening and eject the implantable monitor from the housing; an inserter arranged at and extending from the distal portion of the housing and configured to create a pocket for the implantable monitor within the patient; and a sensor arranged on the inserter and configured to determine an operative position for the implantable monitor within the patient In Example 31, the introducer system of Example 30, wherein the sensor includes one or more electrical contacts configured to interface with one or more electrodes of the implantable monitor and to determine the operative position for the arrangement of the implantable monitor.

In Example 32, the introducer system of Example 31, wherein the sensor is configured to determine a hearth rhythm of the patient using the one or more electrodes of the implantable monitor.

In Example 33, the introducer system of Example 31, further including at least one visual aid arranged on the body portion, and the at least one visual aid is configured to indicate the determination of the operative position by the sensor.

In Example 34, an introducer system for facilitating placement of an implantable monitor, the introducer including: a scalpel; a depth limiter configured to interface with a scalpel to limit a depth of incision for implantation of the implantable monitor within a patient.

In Example 35, the introducer system of Example 34, wherein the depth limiter is configured to surround a blade of the scalpel and control a length of the blade that protrudes through the depth limiter.

While multiple embodiments are disclosed, still other embodiments of the present disclosure will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
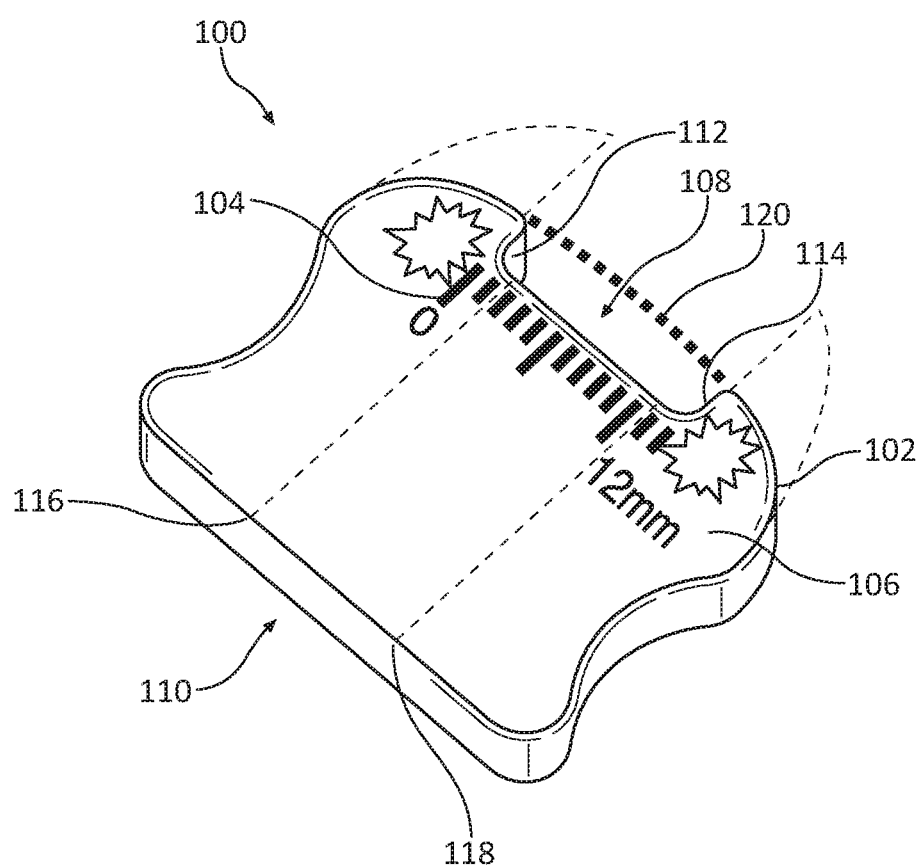
FIG. 1 shows an example introducer for facilitating placement of an implantable monitor in accordance with various aspects of the present disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosed subject matter as characterized by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Implantable monitors may be configured to monitor various physiological parameters and/or provide therapy to a patient. The implantable monitor may be implanted subcutaneously within an implantation location or pocket in the patient's chest or abdomen. Improper implant location may result in the poor acquisition of the physiological parameters and/or the inability to provide therapy. Improper pocket formation may result in an implanted device being ejected from the pocket. Various aspects of the present disclosure are directed toward facilitating placement of an implantable monitor within the patient. For example, various aspects are directed toward facilitating operative pocket formation (e.g., depth, width, length, and angle) and operative pocket location for an implantable monitor.

FIG. 1 shows an example introducer 100 for facilitating placement of an implantable monitor in accordance with various aspects of the present disclosure. The introducer 100 may include a body portion 102 and an indicator cooperating with the body portion 102 and configured to indicate at least one of width, depth, and position for an arrangement of the implantable monitor relative to a patient. As shown in FIG. 1, the introducer 100 may include a width indicator in the form of a measurement scale 104 arranged on an upper surface 106 of the body portion 102. The measurement scale 104 may include a series of marks that provide a visual guide to a clinician making an incision. The measurement scale 104 may have a total width at least approximately equal to a width of the implantable monitor (not shown) that is to be implanted in a patient.

In certain instances, the introducer 100 may include a width indicator in the form of a gap 108. The introducer 100 may include the gap 108 and the measurement scale 104, or one of the gap 108 and the measurement scale 104. In instances where the introducer 100 includes both the gap 108 and the measurement scale 104, as shown in FIG. 1, the gap 108 may have a width that is at least approximately equal to a total width of the measurement scale 104. As noted above, the total width of the measurement scale 104 may be at least approximately equal to the width of the implantable monitor that is to be implanted in the patient. Thus, each of the measurement scale 104 and the gap 108 may be at least approximately equal to the width of the implantable monitor.

The gap 108 may be an opening through each of the upper surface 106 and a lower surface 110 of the body portion 102. In addition, the gap 108 may include a first side wall 112 and a second side wall 114. The first side wall 112 and the second side wall 114 may provide a start and end point for the clinician to make the incision. The clinician may use the gap 108 as a guide for making the incision. In certain instances, the first side wall 112 and the second side wall 114 may provide a maximum width for the body portion 102. The body portion 102 may include different boundaries 116, 118 (represented by the dotted lines) such that the body portion 102 forms a y-shape. In addition, the first side wall 112 and the second side wall 114 may have additional length (illustrated by the dotted lines) to extend the y-shape. In certain instances, the gap 108 may include an upper boundary 120. The upper boundary 120 may form a section of a top surface 122 of the body portion 102. The upper boundary 120 may provide an enclosed section that guides the clinician in making the incision. Thus, the enclosed gap 108 may be configured to limit the width for the arrangement of the implantable monitor by guiding and bounding the clinician in making the incision. The gap 108 limiting the width of the incision may thereby limit the pocket width into which the implantable monitor is to be implanted.

Figure 4:
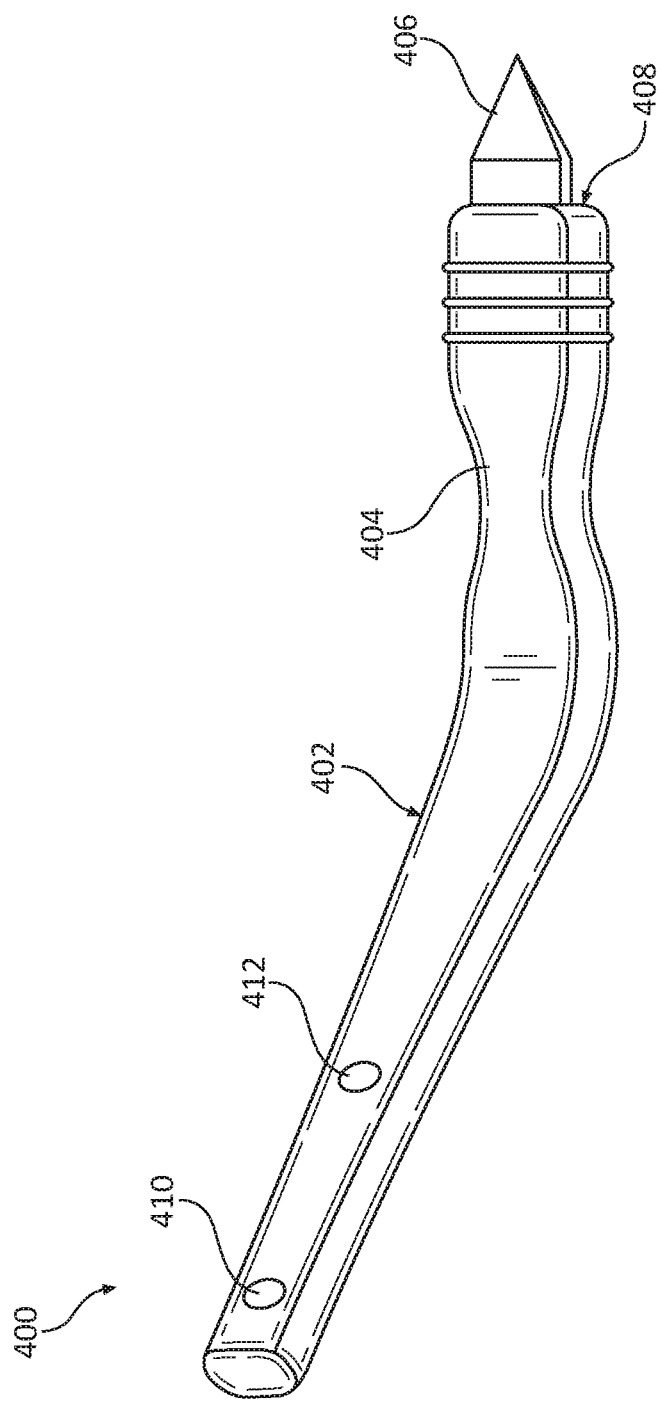
FIG. 4 shows an example cutter for facilitating placement of an implantable monitor in accordance with various aspects of the present disclosure.

The measurement scale 104 and the gap 108 (width indicators) are configured to provide an indication of pocket width to the clinician for implantation of the implantable monitor therein. In certain instances, the gap 108, via the first side wall 112 and the second side wall 114, may be configured to limit the depth for the arrangement of the implantable monitor. The clinician may use a cutter that is configured to interface and cooperate with the introducer 100. The cutter (e.g., as shown in FIG. 4) may include a blade and a surface that surrounds the blade. This surface (e.g., surface 408 shown in FIG. 4) may include a width that is substantially equal to the width of the gap 108. The first side wall 112 and the second side wall 114 may provide a stopping point such that the blade of the tool is prevented from extending into the patient more than a certain depth. Thus, in limiting the depth, the blade may extend into the patient, and the first side wall 112 and the second side wall 114 limit the depth and width of the pocket formation.

In certain instances, the lower surface 110 of the body portion 102 may include a stamp to mark the operative position for the implantable monitor onto skin of a patient. In embodiments, the lower surface 110 may include markings that indent the patient's skin or the lower surface 110 may include ink to make a non-permanent mark that allows the clinician to leave an indication of the desired location for the implantable monitor.

Figure 2:
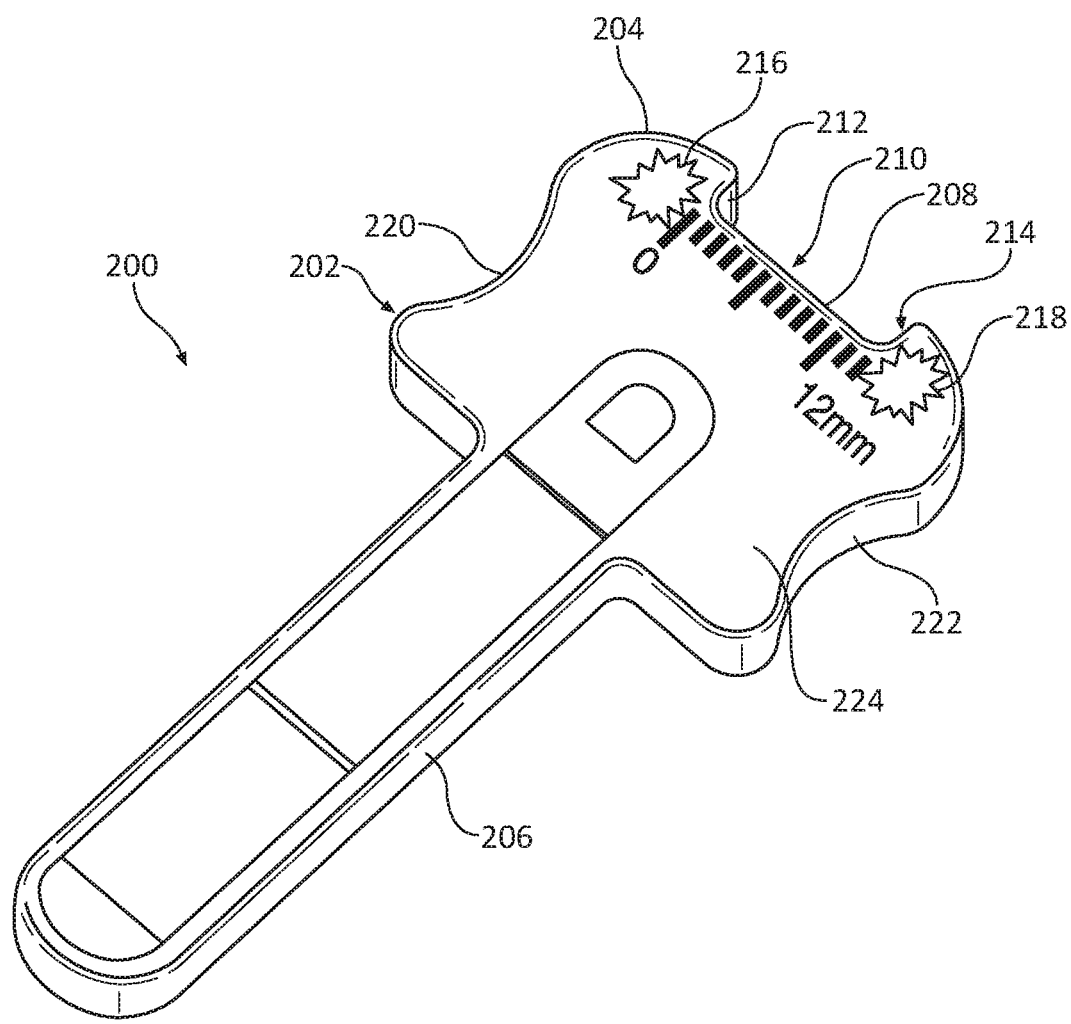
FIG. 2 shows another example introducer for facilitating placement of an implantable monitor in accordance with various aspects of the present disclosure.

FIG. 2 shows another example introducer 200 for facilitating placement of an implantable monitor in accordance with various aspects of the present disclosure. The introducer 200 may include a body portion 202 having a first section 204 and a second section 206. According to embodiments shown in FIG. 2, the second section 206 may be arranged at least approximately perpendicular to a measurement scale 208 of the first section 204. In addition, the second section 206 may have a size and shape equal to a size and shape of the implantable monitor. The introducer 200 may include an indicator cooperating with at least one of the first section 204 and the second section 206 of the body portion 202 that is configured to indicate at least one of width, depth, and position for an arrangement of the implantable monitor relative to a patient.

The introducer 200, as shown in FIG. 2, includes two width indicators in the form of the measurement scale 208 and a gap 210. The measurement scale 208 may include a series of marks that provide a visual guide to a clinician making an incision. The gap 210 may include a first side wall 212 and a second side wall 214 that may indicate to the clinician a starting point and a stopping point for the incision. In addition, the first side wall 212 and the second side wall 214 may effectively limit the incision width by providing the starting and stopping points for the incision The measurement scale 208 and the gap 210 may have a total width at least approximately equal to a width of the implantable monitor (not shown) that is to be implanted in a patient. In addition, the measurement scale 208 and the gap 210 may have a width that is at least approximately equal to the resulting width of the pocket into which the implantable monitor is to be implanted. The measurement scale 208 may include markings every millimeter and have a total width of, for example, between 6 and 14 mm. The measurement scale 208 may include any other total width, markings, and/or the like, which may be configured based on the application for which the introducer 200 is intended.

The measurement scale 208 and the gap 210 (width indicators) are configured to provide an indication of pocket width to the clinician for implantation of the implantable monitor therein. In certain instances, the introducer 200 may include an indicator that is separable from the body portion 202. The separable indicator may be configured to interface and cooperate with the body portion 202. Such a separable indicator (depth limiter) is discussed in further detail with reference to FIGS. 5A-B. For example, the separable indicator (depth limiter) may be arranged around a blade of a scalpel. In this configuration, a surface (surface 508 shown in FIG. 5B) of the separable indicator (depth limiter), shown in FIGS. 5A-B, may contact an upper surface 224 of the body portion 202 at the gap 210. Thus, the gap 210 may be configured to pass the scalpel therethrough and guide the clinician with respect to the width for the incision. The combination of the separable indicator (depth limiter) and the body portion 202 of the introducer 200 may also indicate (and limit) a depth for the incision made by the scalpel. In certain instances, this depth may be the depth of the pocket into which the implantable monitor is to be implanted.

In other instances, a surface (surface 408 shown in FIG. 4) of a cutter used to form the incision, as shown in FIG. 4, may contact the upper surface 224 of the body portion 202 at the gap 210. The gap 210 may limit the depth through which the cutter blade may incise the patient. Thus, the gap 210 may be configured to limit the depth for the incision and control the depth of the pocket.

In certain instances, the introducer 200 may include an indicator that is configured to indicate position for the implantable monitor. In embodiments, this indicator is configured to indicate a location on the patient's torso where the pocket is to be formed. The position indicator may be arranged within the body portion 202 of the introducer 200 and be configured to sense an impedance measurement of the patient. The impedance measurement may be taken on top of the patient's skin. Circuitry arranged within the body portion 202 senses whether the location under the patient's skin would have an impedance indicative of a position having acceptable acquisition of the physiological parameters. For example, the body portion 202 may be moved across the patient's skin where the circuitry arranged within the body portion may sense heart waves (e.g., Electrocardiography). An operative site of implantable may be a site that produces suitably sized (large) R waves while at the same time also having P and T waves that are suitable (small) so as to not produce over-sensing. The suitably sized (large) R waves, for example, may have a value of at least approximately 0.3 mV to approximately 0.7 mV (and more particularly at least 0.4 or 0.5 mV) and the P/T waves may have a value of less than approximately 0.3 mV (and more particularly 0.2 mV). In certain instances, the operative site of implantation may be a site where the values of the R waves are approximately double the values of the P/T waves. The position indicator may provide an indication as to the position for the arrangement of the implantable monitor in response thereto.

The suitable implantation location may be communicated via one or more visual aids 216, 218 arranged with the introducer 200. The visual aids 216, 218 may direct a clinician to an operative position in response to the impedance measurement sensed by the indicator. One of the visual aids 216, 218 may provide a positive indication (green light) that the clinician has the introducer 200 arranged at an operative position, and the other of the visual aids 216, 218 may provide a negative indication (red light) that the clinician has the introducer 200 arranged at an inoperative position. The clinician may move the introducer 200 along the torso of the patient until the visual aids 216, 218 provide a positive indication. According to embodiments, any number of other types of indicators may be used instead of, or in addition to, the lights depicted in FIG. 2. For example, additional lights (e.g., varying degrees of orange and/or yellow lights) may be used to indicate proximity to an operative position. Other types of indicators may include audible indicators, tactile indicators, digital information displays, and/or the like.

As used herein, the terms "operative" and "inoperative" refer to a desired or preferred position—that is, a position at which the operation of the implantable monitor may be disposed to facilitate its operation. For instance, an operative position may refer to a position, region, or set of positions or regions, that is determined to be a position in which the operations of the implantable monitor will be facilitated to a higher degree than if the implantable monitor were placed in another position. Similarly, an inoperative position may refer to a position that is not ideal—that is, a position in which the operations of the implantable monitor are determined to be less facilitated than if the implantable monitor were placed in an operative position. Thus, for example, an "inoperative" position is not meant to necessarily refer to a position in which the implantable monitor cannot operate.

In certain instances, the body portion 202 may include gripping portions 220, 222. The gripping portions 220, 222 may taper inwardly toward a center of the body portion 202. The gripping portions 220, 222 may provide a surface for the clinician to manipulate the introducer 200.

The illustrative components shown in FIG. 2 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 2 may be, in embodiments, integrated with various other components depicted therein (and/or components not illustrated), all of which are considered to be within the ambit of the disclosed subject matter. For example, the body portion 202 may include an upper boundary 120 as shown in FIG. 1.

Figure 3:
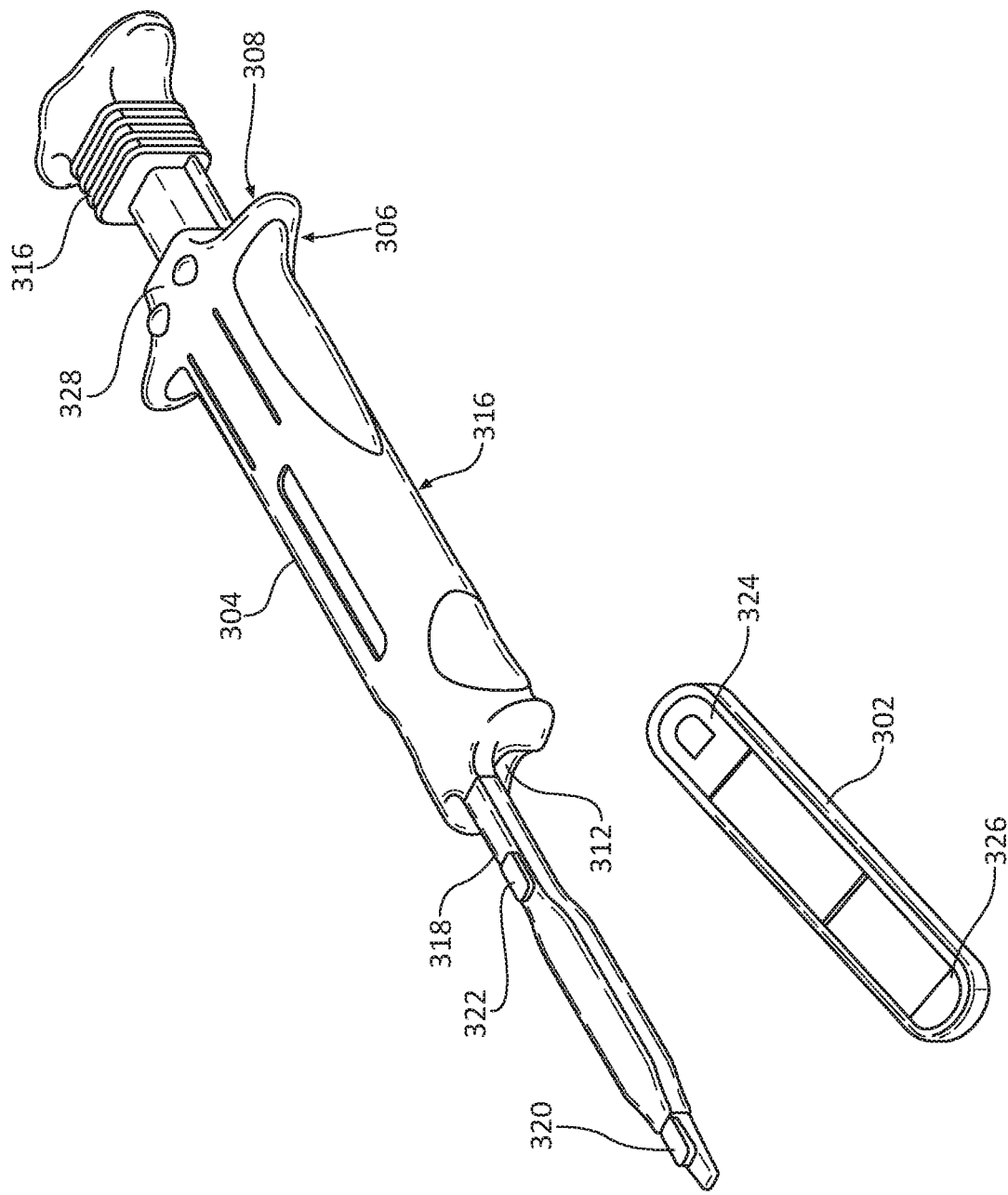
FIG. 3 shows yet another example introducer for facilitating placement of an implantable monitor in accordance with various aspects of the present disclosure.

FIG. 3 shows yet another example introducer 300 for facilitating placement of an implantable monitor 302 in accordance with various aspects of the present disclosure. The introducer 300 includes a body portion 304 having a proximal portion 306 including a proximal opening 308, and a distal portion 310 including a distal opening 312. An intermediate portion 314 separates the proximal portion 306 and the distal portion 310. The intermediate portion 314 is sized and configured to contain the implantable monitor 302.

The introducer 300 is also provided with an ejection rod 316 that is configured to pass through the proximal opening 308, and configured to eject the implantable monitor 302 from the body portion 304. The ejection rod 316 and body portion 304 may function similar to a plunger such that the implantable monitor 302 is ejected from the body portion 304 in response to a user applying force to the ejection rod 316 in a direction that is longitudinally along the body of the ejection rod 316 or at least approximately parallel with the length of the body portion 304.

The introducer 300 also may include an inserter 318 arranged at and extending from the distal portion 310 of the body portion 304. The inserter 318 may be configured to create a pocket sized to surround the implantable monitor 302 within the patient. The implantable monitor 302 may be guided into the pocket in response to the ejection rod 316 ejecting the implantable monitor from the body portion 304 through the distal opening 312. In creating a pocket in a patient, an incision may be made in a patient's skin. The incision may be made by a separate device, or may be made by the inserter 318. After the incision is made, the inserter 318 may be manipulated within the patient through the incision, and the pocket for the implantable monitor 302 is then formed.

In certain instances, the introducer 300 and the implantable monitor 302 may be provided as a system such that the implantable monitor 302 is loaded with the introducer 300. In addition to the introducer 300 and the implantable monitor 302, the system may also include a device for making an incision in a patient. This device for making the incision may be any device having a sharp edge (such as scalpel, shown in FIG. 5B) or a cutter (shown in FIG. 4).

The introducer 300 may also include a sensor (or indicator) arranged on the inserter 318 and configured to determine an operative position for the implantable monitor 302 within the patient. In certain instances, the sensor includes one or more electrical contacts 320, 322. The electrical contacts 320, 322 may be configured to interface with one or more electrodes 324, 326 of the implantable monitor 302 and determine the operative position for the arrangement of the implantable monitor. In embodiments, the circuitry of the sensor (or indicator) may be configured to utilize the implantable monitor 302 to determine whether the implantable monitor 302 is in an operative position. As noted above, the implantable monitor 302 may monitor various physiological parameters. The electrical contacts 320, 322 may electrically couple with the electrodes 324, 326 of the implantable monitor 302, and use the circuitry of the implantable monitor 302 to measure the patient's physiological parameters (e.g., a hearth rhythm of the patient). This measurement may occur when the implantable monitor 302 is implanted in the pocket or when the implantable monitor 302 is on the skin of the patient prior to pocket formation. The sensor may provide an indication as to the arrangement of the implantable monitor in response to the sensing.

An operative site of implantable may be a site that produces suitably sized (large) R waves while at the same time also having P and T waves that are suitable (small) so as to not produce over-sensing. The suitably sized (large) R waves, for example, may have a value of at least approximately 0.3 mV to approximately 0.7 mV (and more particularly at least 0.4 or 0.5 mV) and the P/T waves may have a value of less than approximately 0.3 mV (and more particularly 0.2 mV). In certain instances, the operative site of implantation may be a site where the values of the R waves are approximately double the values of the P/T waves.

For example, the introducer 300 may include a visual aid 328 that directs a clinician to the operative position in response to the impedance measurement sensed by the sensor via the electrodes 324, 326 of the implantable monitor 302. The visual aid 328 may provide a positive indication (green light) when the clinician has the introducer 300 arranged at an operative position, and a negative indication (red light) when the clinician has the introducer 300 arranged at an inoperative position. The clinician may reposition the introducer 300 until the visual aid 328 provides a positive indication. According to embodiments, any number of other types of indicators may be used instead of, or in addition to, the lights depicted in FIG. 3. For example, additional lights (e.g., varying degrees of orange and/or yellow lights) may be used to indicate proximity to an operative position. Other types of indicators may include audible indicators, tactile indicators, digital information displays, and/or the like.

FIG. 4 shows an example cutter 400 for facilitating placement of an implantable monitor in accordance with various aspects of the present disclosure. The cutter 400 may be configured to form an incision in a patient. The cutter 400 may include a first section 402 that allows a clinician to grip the cutter 400. The cutter 400 also includes a second section 404 arranged at an angle relative to the first section 402. The second section 404 includes a blade 406 arranged at an end thereof. The cutter 400 also includes a surface 408 that is configured to limit a depth of the incision. In certain instances, the blade 406 is inserted into the patient such that the second section 404 is at least approximately perpendicular to the skin. The blade 406 will enter the patient until the surface 408 is pressed against the skin. The surface 408 mitigates against the blade 406 inserting further into the skin.

In other instances, the surface 408 may be configured to interface with a body portion of an introducer as noted above with reference to FIG. 2. A gap in the introducer is configured to limit the depth for the incision by allowing the blade 406 to pass therethrough. The surface 408 of the cutter 400 contacts the upper portion of the introducer and limits the depth of the blade 406 incision. The depth of the incision made by the cutter 400 may be a depth of the pocket. Thus, the surface 408 of the cutter 400, in connection with the introducer, indicates a depth of incision and pocket to the clinician by providing a set amount for the blade 406 to incise, and also limit a depth of the incision and pocket.

The cutter 400 may also include electrical contacts 410, 412. The electrical contacts 410, 412 may be configured to interface with one or more electrodes of the implantable monitor and facilitate determining the operative position for the arrangement of the implantable monitor. In embodiments, the cutter 400 may include circuitry configured to utilize the implantable monitor to determine whether the implantable monitor is in an operative position. The electrical contacts 410, 412 may electrically couple with the electrodes of the implantable monitor, and use the circuitry of the implantable monitor to measure the patient's physiological parameters (e.g., a hearth rhythm of the patient). This measurement may occur when the implantable monitor is implanted in the pocket or when the implantable monitor is on the skin of the patient prior to pocket formation. The cutter 400 may provide an indication as for the arrangement of the implantable monitor in response to the sensing by the electrical contacts 410, 412 and the implantable monitor. The cutter 400 may include a visual aid (as discussed above with reference to FIG. 2 and FIG. 3) to assist in the positional indication.

The operative site of implantable may be a site that produces suitably sized (large) R waves while at the same time also having P and T waves that are suitable (small) so as to not produce over-sensing. The suitably sized (large) R waves, for example, may have a value of at least approximately 0.3 mV to approximately 0.7 mV (and more particularly at least 0.4 or 0.5 mV) and the P/T waves may have a value of less than approximately 0.3 mV (and more particularly 0.2 mV). In certain instances, the operative site of implantation may be a site where the values of the R waves are approximately double the values of the P/T waves.

Figure 5A:
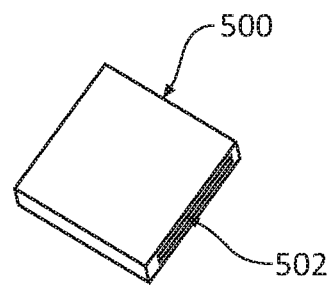
FIG. 5A shows an example depth limiter for facilitating placement of an implantable monitor in accordance with various aspects of the present disclosure.

FIG. 5A shows an example depth limiter 500 for facilitating placement of an implantable monitor in accordance with various aspects of the present disclosure. The depth limiter 500 may be used as an introducer for facilitating placement of an implantable monitor. The depth limiter 500 may include an aperture 502 that allows a blade of a scalpel to pass partially therethrough as is shown in FIG. 5B.

Figure 5B:
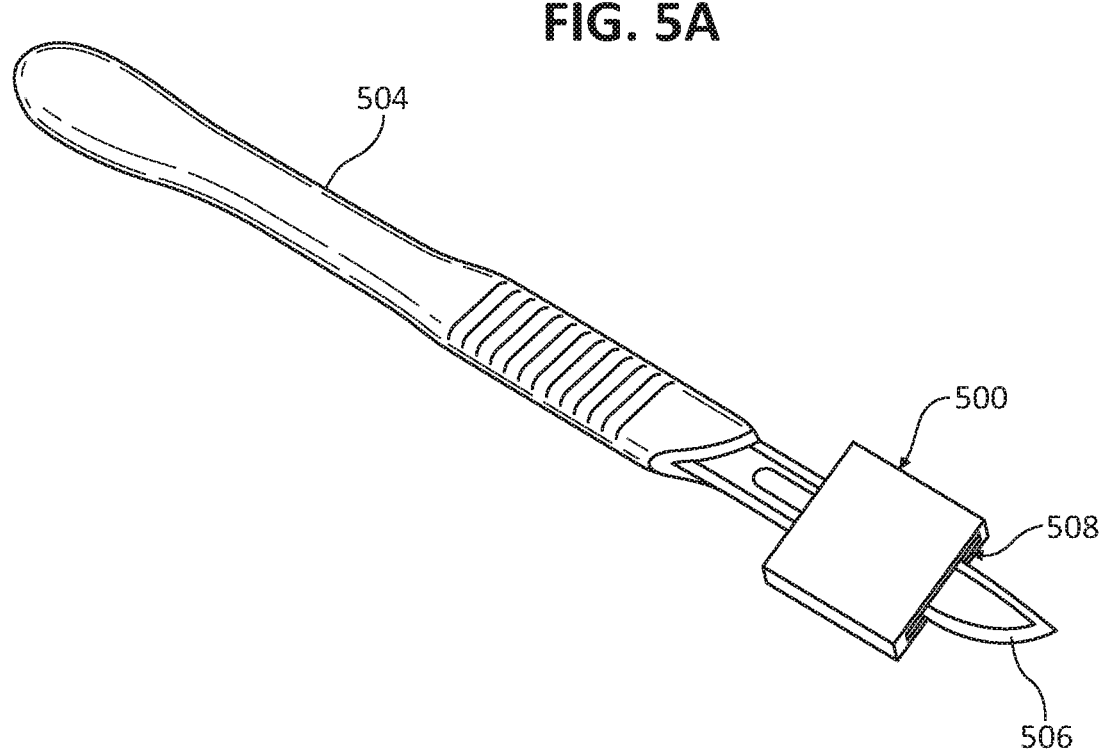
FIG. 5B shows the depth limiter for facilitating placement of an implantable monitor implantable monitor, shown in FIG. 5A, arranged with a scalpel in accordance with various aspects of the present disclosure.

FIG. 5B shows the depth limiter 500 for facilitating placement of an implantable monitor implantable monitor, shown in FIG. 5A, arranged with a scalpel 504 in accordance with various aspects of the present disclosure. The depth limiter 500 is configured to interface with the scalpel 504 to limit a depth of incision for implantation of the implantable monitor within a patient. As shown in FIG. 5B, the depth limiter 500 is configured to surround the blade 506 of the scalpel 504 and control a length of the blade 506 that protrudes through the depth limiter 500. The depth limiter 500 may have a friction fit with the blade 506. In embodiments, the aperture 502 of the depth limiter 500 may have a width that stops the depth limiter 500 at a certain point on the blade 506. The aperture 502 of the depth limiter 500 may taper inwardly to provide the stopping point. The aperture 502 of the depth limiter 500 may be configured based on the type of blade 506 of the scalpel 504 (e.g., 10 blade, 11 blade, etc.)

In addition, a surface 508 of the depth limiter 500 may be configured to interface with a body portion of an introducer as noted above with reference to FIG. 2. A gap in the introducer is configured to limit the depth for the incision by allowing the blade 506 to pass therethrough. The surface 508 of the depth limiter 500 contacts the upper portion of the body portion at the gap and limits the depth of the blade 506 incision. The depth of the incision made by the depth limiter 500 may be a depth of the pocket. Thus, the surface 508 of the depth limiter 500, in connection with the body portion of the introducer, indicates a depth of incision and pocket to the clinician by providing a set amount for the blade 506 to incise, and also limit a depth of the incision and pocket.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An introducer for facilitating placement of an implantable monitor, the introducer comprising:
a body portion having gripping portions on opposite sides of the body portion having at least a portion tapering inwardly toward a center of the body portion; and
an indicator cooperating with the body portion and including a gap configured to guide at least one of a width for an incision into the skin of a patient and depth of an incision for the incision within the patient and configured to sense an impedance measurement of the patient and indicate a position for the implantable monitor within the patient while being positioned on a surface of skin of the patient.

2. The introducer of claim 1, wherein the indicator comprises a measurement scale arranged on an upper surface of the body portion, and the measurement scale indicates the width for the incision for the arrangement of the implantable monitor within the patient.

3. The introducer of claim 2, wherein the indicator comprises the gap on the body portion arranged between a first side wall and a second side wall, and the gap is configured to limit the width for the incision for the arrangement of the implantable monitor within the patient.

4. The introducer of claim 3, wherein the gap comprises an upper boundary, and the upper boundary forms a portion of a top surface of the body portion.

5. The introducer of claim 4, wherein the gap is configured to limit the depth for the incision and the width for the incision for the arrangement of the implantable monitor within the patient.

6. The introducer of claim 5, wherein the gap is configured to pass a scalpel therethrough and guide the depth for the incision and the width for the incision.

7. The introducer of claim 1, further comprising at least one visual aid arranged on an upper surface of the body portion, and the at, least, one visual aid is configured to direct a clinician to move the implantable monitor to an operative position in response to the impedance measurement sensed by the indicator.

8. The introducer of claim 1, wherein the body portion comprises a first section and a second section, the first section including at least one of the gripping portions tapering inwardly toward a center of the body portion.

9. The introducer of claim 1, wherein the gripping portions include a first section tapering inwardly toward the center of the body portion and a second section tapering away from the center of the body portion.

10. The introducer of claim 1, wherein, the indicator includes a sensor having at least one electrical contact, the implantable monitor includes at least, one electrode, and the at least one electrical contact of the indicator is configured for interfacing with the at least one electrode of the implantable monitor.

11. An introducer for facilitating placement of an implantable monitor, the introducer comprising:
a body portion; and
an indicator cooperating with the body portion and including a gap configured to guide either a width for an incision into the skin of a patient or a depth of the incision within the patient and configured to sense an impedance measurement of the patient and indicate a position for the implantable monitor within the patient while being positioned on a surface of skin of the patient.

12. The introducer of claim 11, wherein the indicator includes a sensor having an electrical contact.

13. The introducer of claim 12, wherein the electrical contact of the indicator is configured for interfacing with an electrode of the implantable monitor.

* * * * *